(12) United States Patent
Wang et al.

(10) Patent No.: US 8,814,931 B2
(45) Date of Patent: Aug. 26, 2014

(54) STAGED DEPLOYMENT DEVICES AND METHODS FOR TRANSCATHETER HEART VALVE DELIVERY SYSTEMS

(75) Inventors: Huisun Wang, Maple Grove, MN (US); Ralph Joseph Thomas, Champlin, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 46 days.

(21) Appl. No.: 13/212,442

(22) Filed: Aug. 18, 2011

(65) Prior Publication Data

US 2012/0078352 A1 Mar. 29, 2012

Related U.S. Application Data

(60) Provisional application No. 61/376,425, filed on Aug. 24, 2010.

(51) Int. Cl.
*A61F 2/24* (2006.01)
(52) U.S. Cl.
USPC .......................................... 623/2.11; 606/108
(58) Field of Classification Search
USPC .............. 623/1.11, 1.12, 1.23, 2.11; 606/108, 606/191, 192, 194
See application file for complete search history.

(56) References Cited

U.S. PATENT DOCUMENTS

| | | | |
|---|---|---|---|
| 3,657,744 A | 4/1972 | Ersek | |
| 4,275,469 A | 6/1981 | Gabbay | |
| 4,491,986 A | 1/1985 | Gabbay | |
| 4,759,758 A | 7/1988 | Gabbay | |
| 4,922,905 A | 5/1990 | Strecker | |
| 5,391,172 A | 2/1995 | Williams et al. | |
| 5,411,552 A | 5/1995 | Andersen et al. | |
| 5,456,667 A | 10/1995 | Ham et al. | |
| 5,480,423 A | 1/1996 | Ravenscroft et al. | |

(Continued)

FOREIGN PATENT DOCUMENTS

| | | |
|---|---|---|
| AU | 2011202175 B1 | 7/2011 |
| DE | 19857887 A1 | 7/2000 |

(Continued)

OTHER PUBLICATIONS

International Search Report Application No. PCT/US2011/048963, dated Dec. 15, 2011.

(Continued)

*Primary Examiner* — Dianne Dornbusch
*Assistant Examiner* — Robert Lynch
(74) *Attorney, Agent, or Firm* — Lerner, David, Littenberg, Krumholz & Mentlik, LLP

(57) ABSTRACT

A delivery device for a collapsible heart valve includes an operating handle, including a frame defining a movement space therein, a carriage assembly moveable within the movement space, and a first resheathing lock having a locked position and an unlocked position. The delivery device further includes a catheter assembly, including a first shaft around which a valve-receiving compartment is defined, the first shaft being fixedly connected to one of the frame or the carriage assembly, and a distal sheath operatively connected to the carriage assembly. The distal sheath is moveable between a closed condition adapted to maintain the valve in the compartment and an open condition adapted to fully deploy the valve. With the resheathing lock in the locked position, the distal sheath is unable to move to the open condition to fully deploy the valve.

19 Claims, 8 Drawing Sheets

(56) References Cited

U.S. PATENT DOCUMENTS

| | | |
|---|---|---|
| 5,843,167 A | 12/1998 | Dwyer et al. |
| 5,935,163 A | 8/1999 | Gabbay |
| 5,961,549 A | 10/1999 | Nguyen et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,719,789 B2 | 4/2004 | Cox |
| 6,730,118 B2 | 5/2004 | Spenser et al. |
| 6,736,845 B2 | 5/2004 | Marquez et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,311,730 B2 | 12/2007 | Gabbay |
| 7,329,278 B2 | 2/2008 | Seguin et al. |
| 7,374,573 B2 | 5/2008 | Gabbay |
| 7,381,218 B2 | 6/2008 | Schreck |
| 7,399,315 B2 | 7/2008 | Iobbi |
| 7,452,371 B2 | 11/2008 | Pavcnik et al. |
| 7,476,244 B2 * | 1/2009 | Buzzard et al. ............... 623/1.11 |
| 7,510,572 B2 | 3/2009 | Gabbay |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,353,955 B2 | 1/2013 | Styrc et al. |
| 2002/0036220 A1 | 3/2002 | Gabbay |
| 2002/0183827 A1 | 12/2002 | Derus et al. |
| 2003/0050694 A1 | 3/2003 | Yang et al. |
| 2003/0130726 A1 | 7/2003 | Thorpe et al. |
| 2003/0144725 A1 | 7/2003 | Lombardi |
| 2004/0039436 A1 | 2/2004 | Spenser et al. |
| 2004/0049262 A1 | 3/2004 | Obermiller et al. |
| 2004/0093075 A1 | 5/2004 | Kuehne |
| 2004/0148009 A1 | 7/2004 | Buzzard et al. |
| 2004/0210304 A1 | 10/2004 | Seguin et al. |
| 2004/0260390 A1 | 12/2004 | Sarac et al. |
| 2005/0004583 A1 | 1/2005 | Oz et al. |
| 2005/0049667 A1 | 3/2005 | Arbefeuille et al. |
| 2005/0096726 A1 | 5/2005 | Sequin et al. |
| 2005/0137695 A1 | 6/2005 | Salahieh et al. |
| 2005/0137697 A1 | 6/2005 | Salahieh et al. |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0173532 A1 | 8/2006 | Flagle et al. |
| 2006/0206202 A1 | 9/2006 | Bonhoeffer et al. |
| 2006/0241744 A1 | 10/2006 | Beith |
| 2006/0259120 A1 | 11/2006 | Vongphakdy et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0282150 A1 | 12/2006 | Olson et al. |
| 2006/0282157 A1 | 12/2006 | Hill et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0156225 A1 | 7/2007 | George et al. |
| 2007/0213813 A1 | 9/2007 | Von Segesser et al. |
| 2007/0244545 A1 | 10/2007 | Birdsall et al. |
| 2007/0244552 A1 | 10/2007 | Salahieh et al. |
| 2007/0260301 A1 * | 11/2007 | Chuter et al. ............... 623/1.11 |
| 2007/0288087 A1 | 12/2007 | Fearnot et al. |
| 2008/0004688 A1 | 1/2008 | Spenser et al. |
| 2008/0009940 A1 | 1/2008 | Cribier |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147179 A1 | 6/2008 | Cai et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0228264 A1 | 9/2008 | Li et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269878 A1 | 10/2008 | Iobbi |
| 2008/0269879 A1 | 10/2008 | Sathe et al. |
| 2009/0112309 A1 | 4/2009 | Jaramillo et al. |
| 2009/0118826 A1 | 5/2009 | Khaghani |
| 2009/0138079 A1 | 5/2009 | Tuval et al. |
| 2009/0287299 A1 | 11/2009 | Tabor et al. |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0049313 A1 | 2/2010 | Alon et al. |
| 2010/0082094 A1 | 4/2010 | Quadri et al. |
| 2010/0087907 A1 | 4/2010 | Lattouf |
| 2010/0114305 A1 | 5/2010 | Kang et al. |
| 2010/0121434 A1 * | 5/2010 | Paul et al. ............... 623/2.11 |
| 2010/0131055 A1 | 5/2010 | Case et al. |
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0208298 A1 | 8/2011 | Tuval et al. |
| 2011/0282425 A1 | 11/2011 | Dwork |
| 2012/0197391 A1 | 8/2012 | Alkhatib et al. |

FOREIGN PATENT DOCUMENTS

| | | |
|---|---|---|
| DE | 20000659 U1 | 5/2001 |
| DE | 10121210 A1 | 11/2002 |

(56) References Cited

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| FR | 2847800 A1 | 6/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 0069368 A2 | 11/2000 |
| WO | 0128459 A1 | 4/2001 |
| WO | 0149213 A2 | 7/2001 |
| WO | 0154625 A1 | 8/2001 |
| WO | 0156500 A2 | 8/2001 |
| WO | 0176510 A2 | 10/2001 |
| WO | 0236048 A1 | 5/2002 |
| WO | 0247575 A2 | 6/2002 |
| WO | 03047468 A1 | 6/2003 |
| WO | 2006073626 A2 | 7/2006 |
| WO | 2007071436 A2 | 6/2007 |
| WO | 2008042266 A2 | 4/2008 |
| WO | 2008070797 A2 | 6/2008 |
| WO | 2008138584 A1 | 11/2008 |
| WO | 2009029199 A1 | 3/2009 |
| WO | 2009/042196 A2 | 4/2009 |
| WO | 2009/091509 A1 | 7/2009 |
| WO | 2010008548 A2 | 1/2010 |
| WO | 2010008549 A1 | 1/2010 |
| WO | 2010096176 A1 | 8/2010 |
| WO | 2010098857 A1 | 9/2010 |
| WO | 2012026965 A2 | 3/2012 |
| WO | 2012036741 A2 | 3/2012 |

OTHER PUBLICATIONS

International Search Report Application No. PCT/US2011/048967, dated Dec. 15, 2011.
International Search Report Application No. PCT/US2011/048989, dated Dec. 15, 2011.
Australian Examination Report for Application No. 2011293898 dated Jul. 26, 2013
Commonly owned co-pending U.S. Appl. No. 13/216,124, filed Aug. 23, 2011.
Commonly owned co-pending U.S. Appl. No. 13/234,782, filed Sep. 16, 2011.
Commonly owned co-pending U.S. Appl. No. 13/788,820, filed Mar. 7, 2013
International Search Report and Written Opinion for Application No. PCT/US2011/001450 dated Mar. 5, 2012.
International Search Report and Written Opinion for Application No. PCT/US2011/001615 dated Jul. 11, 2012.
Overview of PRE-CE Mark Transcatheter Aortic Valve Technologies (powerpoint—dated Jun. 1, 2010).
International Search Report for Application No. PCT/US2011/001597 dated Mar. 7, 2012.

* cited by examiner

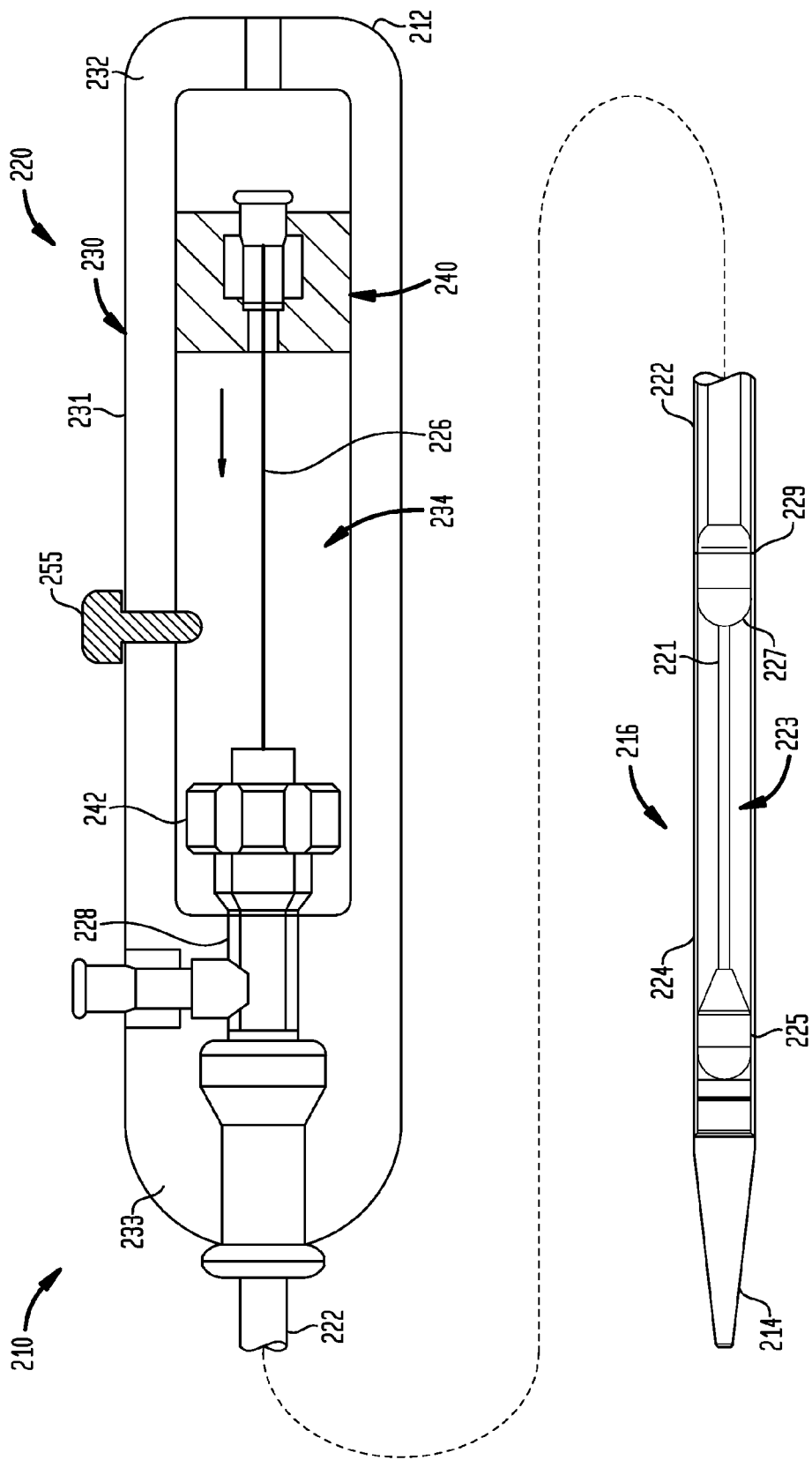

STAGED DEPLOYMENT DEVICES AND METHODS FOR TRANSCATHETER HEART VALVE DELIVERY SYSTEMS

CROSS-REFERENCE TO RELATED APPLICATIONS

This application claims the benefit of the filing date of U.S. Provisional Patent Application No. 61/376,425 filed Aug. 24, 2010, the disclosure of which is hereby incorporated herein by reference.

BACKGROUND OF THE INVENTION

The present invention is related to prosthetic heart valve replacement, and more particularly to devices, systems, and methods for transcatheter delivery of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

In conventional delivery systems for self-expanding aortic valves, for example, after the delivery system has been positioned for deployment, the annulus end of the valve is typically unsheathed and expanded first, while the aortic end of the valve remains sheathed. Once the annulus end of the valve has expanded, it may be determined that the valve needs to be repositioned in the patient's aortic annulus. To accomplish this, a user (such as a surgeon or an interventional cardiologist) typically resheathes the annulus end of the valve, so that the valve can be repositioned while in a collapsed state. After the valve has been repositioned, the surgeon can again release the valve.

Once a self-expanding valve has been fully deployed, it expands to a diameter larger than that of the sheath that previously contained the valve in the collapsed condition, making resheathing impossible, or difficult at best. In order for the user to be able to resheathe a partially-deployed valve, a portion of the valve must still be collapsed inside of the sheath.

Despite the various improvements that have been made to the collapsible prosthetic heart valve delivery process, conventional delivery devices, systems, and methods suffer from some shortcomings. For example, in conventional delivery devices for self-expanding valves, it is difficult to control how much of the valve remains in the sheath during a partial deployment, and the user may accidentally deploy the valve fully before verifying that the annulus end of the valve is in the optimal position in the patient's valve annulus, thereby taking away the opportunity to resheathe and reposition the valve.

There therefore is a need for further improvements to the devices, systems, and methods for transcatheter delivery of collapsible prosthetic heart valves, and in particular, self-expanding prosthetic heart valves. Among other advantages, the present invention may address one or more of these needs.

BRIEF SUMMARY OF THE INVENTION

A delivery device for a collapsible prosthetic heart valve, a system for delivery of a collapsible prosthetic heart valve, and a method of delivering a collapsible prosthetic heart valve in a patient are disclosed.

A delivery device for a collapsible prosthetic heart valve includes an operating handle, including a frame defining a movement space therein, a carriage assembly moveable in a longitudinal direction within the movement space, and a first resheathing lock having a locked position and an unlocked position, the first resheathing lock in the locked position limiting movement of the carriage assembly in the longitudinal direction to a first intermediate position in the movement space, and the first resheathing lock in the unlocked position permitting movement of the carriage assembly in the longitudinal direction beyond the first intermediate position in the movement space. The delivery device also includes a catheter assembly, including a first shaft around which a compartment is defined, the first shaft being fixedly connected to one of the frame or the carriage assembly, the compartment being adapted to receive the valve in an assembled condition, and a distal sheath operatively connected to the carriage assembly, the distal sheath being moveable between a closed condition adapted to maintain the valve in the assembled condition and an open condition adapted to fully deploy the valve, wherein movement of the carriage assembly to the first intermediate position moves the distal sheath to a condition between the closed condition and the open condition so that the valve is not fully deployed.

The first shaft may be fixedly connected to the frame, the catheter assembly further including an outer shaft connecting the carriage assembly to the distal sheath and at least partially surrounding the first shaft. The first shaft may be fixedly connected to the carriage assembly, and the catheter assembly may further include an outer shaft connecting the frame to the compartment and at least partially surrounding the first shaft. The operating handle may further include a deployment lock moveable between a locked position and an unlocked position, the deployment lock in the locked position preventing movement of the carriage assembly in the longitudinal direction within the movement space, the deployment lock in the unlocked position permitting movement of the carriage assembly in the longitudinal direction within the movement space. The carriage assembly may include a threaded rod and the operating handle may further include a deployment actuator threadedly engaged with the threaded rod such that rotation of the deployment actuator moves the carriage assembly in the longitudinal direction in the movement space.

The compartment may define a first length and the first intermediate position in the movement space may correspond to a travel distance of the carriage assembly, the travel distance being less than the first length. The collapsible prosthetic heart valve may define a second length and the travel distance may be about 80% to about 90% of the second length. The operating handle may further include a second resheathing lock moveable between a locked position and an unlocked position, the second resheathing lock in the locked position limiting movement of the carriage assembly in the longitudinal direction to a second intermediate position in the movement space, the second resheathing lock in the unlocked position permitting movement of the carriage assembly in the longitudinal direction beyond the second intermediate position. The collapsible prosthetic heart valve may define a length, the second intermediate position may define a first travel distance, and the first intermediate position may define a second travel distance, the first travel distance being about 40% to about 60% of the length and the second travel distance being about 80% to about 90% of the length. The frame may include a slot and the first resheathing lock may include a retractable locking member that is engaged in the slot when the first resheathing lock is in the locked position, an end of the slot defining the first intermediate position.

A system for delivery of a collapsible prosthetic heart valve includes a collapsible prosthetic heart valve, and an operating handle, including a frame defining a movement space therein, a carriage assembly moveable in a longitudinal direction within the movement space, and a first resheathing lock having a locked position and an unlocked position, the resheathing lock in the locked position limiting movement of the carriage assembly in the longitudinal direction to a first intermediate position in the movement space, and the first resheathing lock in the unlocked position permitting movement of the carriage assembly in the longitudinal direction beyond the first intermediate position in the movement space. The system also includes a catheter assembly, including a first shaft around which a compartment is defined, the first shaft being fixedly connected to one of the frame or the carriage assembly, the valve being mounted in the compartment in an assembled condition, and a distal sheath operatively connected to the carriage assembly, the distal sheath being moveable between a closed condition adapted to maintain the valve in the assembled condition and an open condition adapted to fully deploy the valve, wherein movement of the carriage assembly to the first intermediate position moves the distal sheath to a condition between the closed condition and the open condition so that the valve is not fully deployed.

The collapsible prosthetic heart valve may define a length and the first intermediate position in the movement space may correspond to a travel distance of the carriage assembly, the travel distance being about 80% to about 90% of the length. The operating handle may further include a second resheathing lock moveable between a locked position and an unlocked position, the second resheathing lock in the locked position limiting movement of the carriage assembly in the longitudinal direction to a second intermediate position in the movement space, the second resheathing lock in the unlocked position permitting movement of the carriage assembly in the longitudinal direction beyond the second intermediate position. The collapsible prosthetic heart valve may define a length, the second intermediate position may define a first travel distance, and the first intermediate position may define a second travel distance, the first travel distance being about 40% to about 60% of the length and the second travel distance being about 80% to about 90% of the length.

A method of delivering a collapsible prosthetic heart valve in a patient includes providing a delivery device having a catheter assembly and an operating handle, the catheter assembly including a compartment adapted to receive the valve in an assembled condition, the operating handle including a frame defining a movement space therein, a carriage assembly moveable in a longitudinal direction within the movement space, and a resheathing lock having a locked position limiting movement of the carriage assembly in the longitudinal direction to a first intermediate position in the movement space and an unlocked position permitting movement of the carriage assembly in the longitudinal direction beyond the first intermediate position in the movement space. The method also includes loading the valve into the compartment of the catheter assembly, the compartment and the valve being covered by a distal sheath of the catheter assembly, inserting the catheter assembly into the patient, positioning the valve at a target location within the patient, using the operating handle to partially deploy the valve by moving the carriage assembly in the longitudinal direction to the first intermediate position in the movement space, moving the resheathing lock from the locked position to the unlocked position, and using the operating handle to fully deploy the valve by moving the carriage assembly in the longitudinal direction beyond the first intermediate position in the movement space.

The target location within the patient may be the native aortic annulus of the patient. The distal sheath of the delivery device may be inserted through a femoral artery of the patient. The distal sheath of the delivery device may be inserted through the apex of the heart of the patient. The step of using an operating handle to partially deploy the valve may include rotating a deployment actuator to move the carriage assembly in the longitudinal direction. The method may also include unlocking a deployment lock to release the carriage assembly for movement in the longitudinal direction. The valve may define a length, the intermediate position may define a longitudinal travel distance, and the step of using an operating handle to partially deploy the valve may include moving the carriage assembly through the travel distance, the travel distance being about 80% to about 90% of the length of the valve.

BRIEF DESCRIPTION OF THE DRAWINGS

Various embodiments of the present invention will now be described with reference to the appended drawings. It is appreciated that these drawings depict only some embodiments of the invention and are therefore not to be considered limiting of its scope.

FIG. 12 is a diagrammatic top plan view of an operating handle for a transapical delivery device for a collapsible prosthetic heart valve, shown with a top plan view of the distal portion of a transapical catheter assembly.

DETAILED DESCRIPTION

Figure 1:
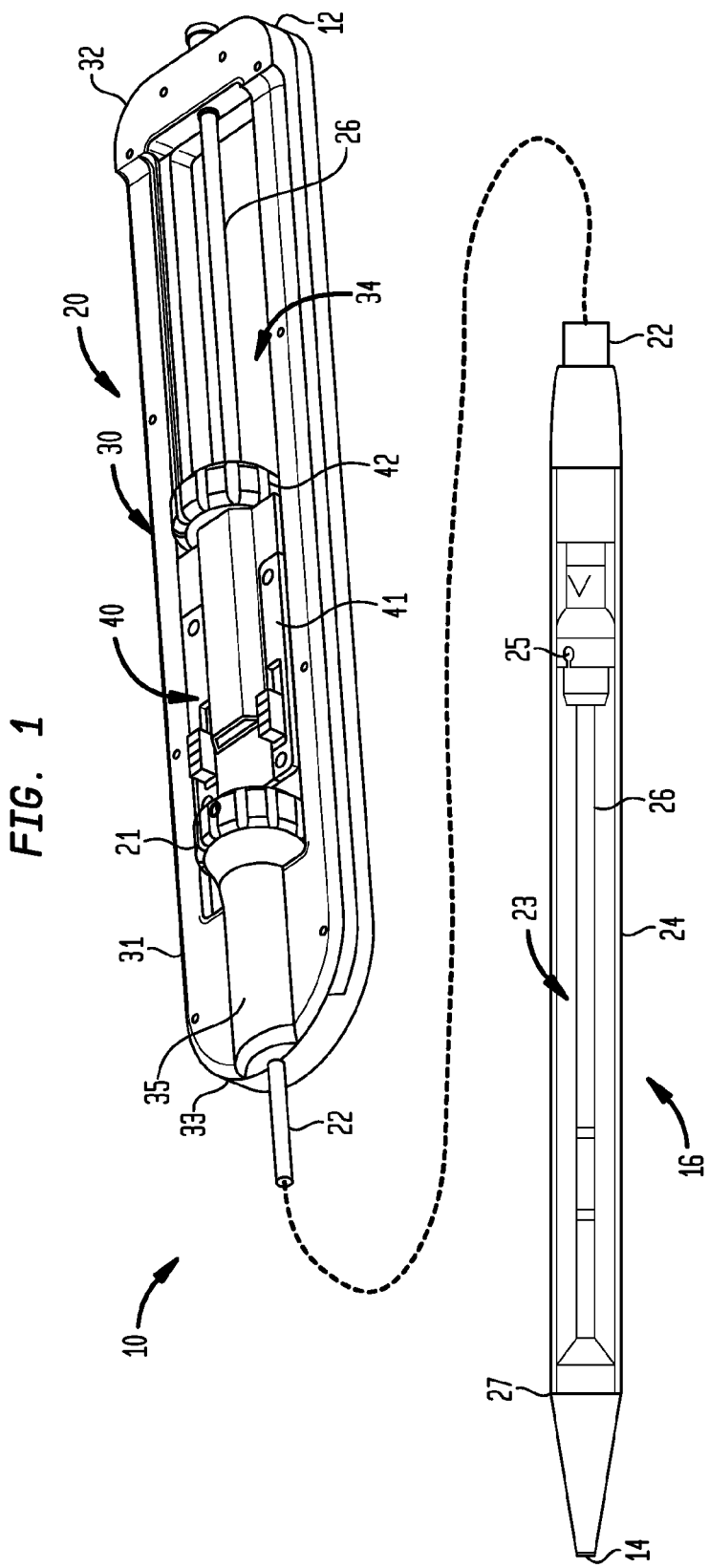
FIG. 1 is a perspective view of an operating handle for a transfemoral delivery device for a collapsible prosthetic heart valve, shown with a side elevation of the distal portion of a transfemoral catheter assembly.
Figure 2:
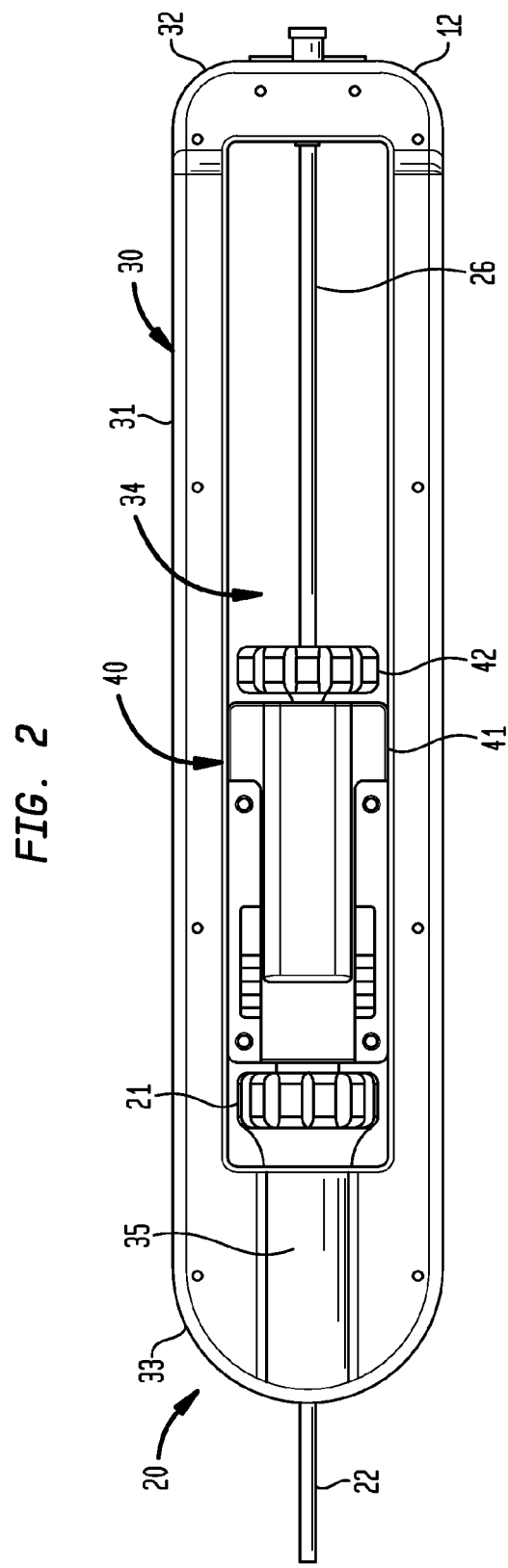
FIG. 2 is a top plan view of the handle of FIG. 1.
Figure 3:
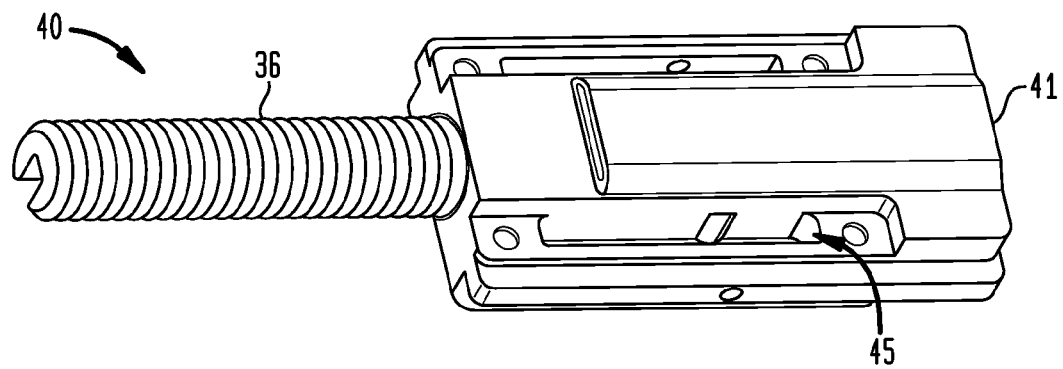
FIG. 3 is an enlarged perspective view of the inner assembly of the handle shown in FIG. 1.
Figure 4:
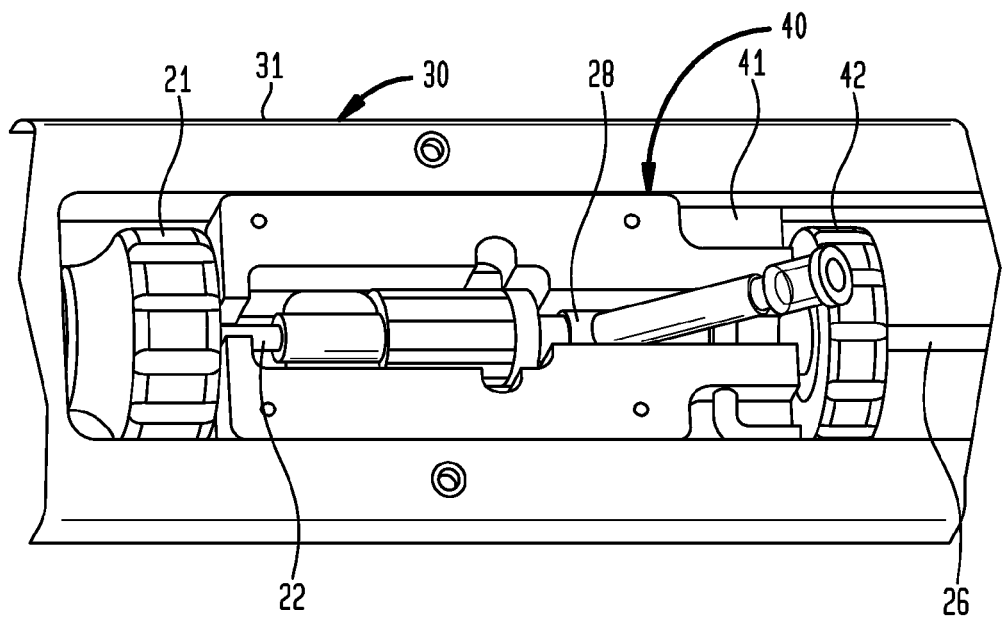
FIG. 4 is an enlarged bottom perspective view of a portion of the handle of FIG. 1.

As used herein, the terms "proximal" and "distal" are to be taken as relative to a user using the disclosed delivery devices. "Proximal" is to be understood as relatively close to the user and "distal" is to be understood as relatively farther away from the user.

Referring now to FIGS. 1-4 to illustrate the structure and function of the present invention, an exemplary transfemoral delivery device 10 for a collapsible prosthetic heart valve (or other types of self-expanding collapsible stents) has a catheter assembly 16 for delivering the heart valve to and deploying the heart valve at a target location, and an operating handle 20 for controlling deployment of the valve from the catheter assembly. The delivery device 10 extends from a proximal end 12 to a distal tip 14. The catheter assembly 16 is adapted to receive a collapsible prosthetic heart valve (not shown) in a compartment 23 defined around an inner shaft 26 and covered by a distal sheath 24.

The inner shaft 26 extends through the operating handle 20 to the distal tip 14 of the delivery device, and includes a retainer 25 affixed thereto at a spaced distance from distal tip 14 and adapted to hold a collapsible prosthetic valve in the compartment 23.

The distal sheath 24 surrounds the inner shaft 26 and is slidable relative to the inner shaft such that it can selectively cover or uncover the compartment 23. The distal sheath 24 is affixed at its proximal end to an outer shaft 22, the proximal end of which is connected to the operating handle 20 in a manner to be described. The distal end 27 of the distal sheath 24 abuts the distal tip 14 when the distal sheath is fully covering the compartment 23, and is spaced apart from the distal tip 14 when the compartment 23 is at least partially uncovered.

The operating handle 20 is adapted to control deployment of a prosthetic valve located in the compartment 23 by permitting a user to selectively slide the outer shaft 22 proximally or distally relative to the inner shaft 26, thereby respectively uncovering or covering the compartment with the distal sheath 24. The proximal end of the inner shaft 26 is affixed to an outer frame 30 of the operating handle 20, and the proximal end of the outer shaft 22 is affixed to a carriage assembly 40 of the operating handle that is slidable along a longitudinal axis of the frame, such that a user can selectively slide the outer shaft relative to the inner shaft by sliding the carriage assembly relative to the frame.

A hemostasis valve 28 (shown, for example, in FIG. 4) includes an internal gasket adapted to create a seal between the inner shaft 26 and the proximal end of the outer shaft 22. A gasket adjustment wheel 42 in the carriage assembly 40 is adapted to adjust the strength of this seal. For example, the gasket inside the hemostasis valve 28 may be in the shape of an O-ring located around the inner shaft 26. When the strength of the seal is insufficient, there may be a gap between the O-ring and the outer surface of the inner shaft 26. To eliminate this gap, a user can turn the gasket adjustment wheel 42 to place a compressive force on the O-ring in the longitudinal direction of the inner shaft 26, thereby compressing the O-ring longitudinally and expanding the O-ring radially. The radially-expanded O-ring can fill the gap between the O-ring and the outer surface of the inner shaft 26, thereby creating a liquid-proof seal therebetween.

Figure 5:
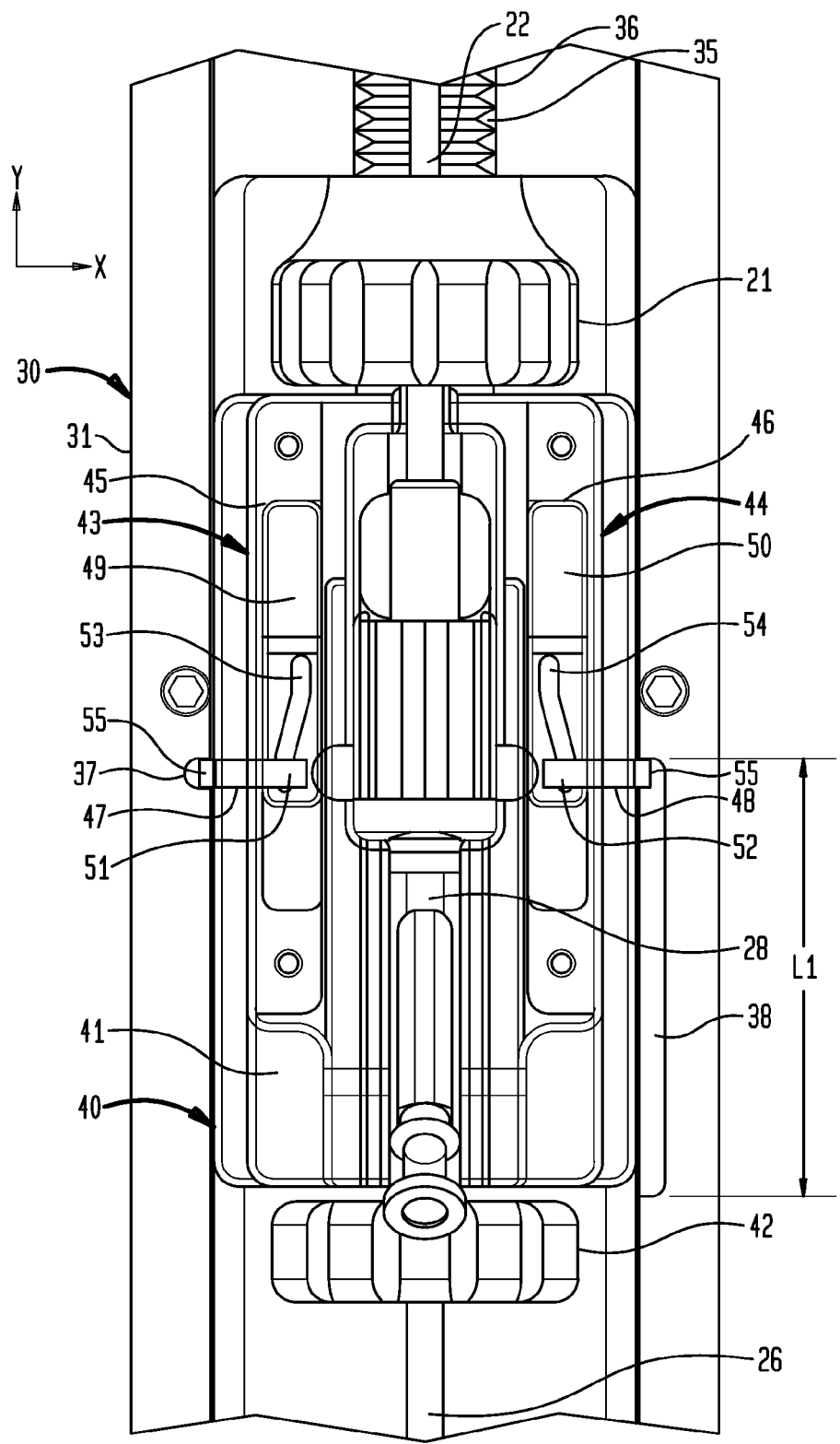
FIG. 5 is an enlarged bottom plan view of the portion of the handle shown in FIG. 4, shown with a transparent inner assembly.

The frame 30 includes a pair of side rails 31 joined at the proximal end 12 by a proximal end member 32 and joined at the distal end by a distal end member 33. Collectively, the side rails 31, the end member 32, and the end member 33 define an elongated space 34 in the frame 30 in which the carriage assembly 40 may travel. The elongated space 34 preferably permits the carriage assembly 40 to travel a distance that is at least as long as the anticipated length of the prosthetic valve to be delivered (e.g., at least about 50 mm), such that the distal sheath 24 can be fully retracted off of the prosthetic valve. An enlarged bore 35 in the end member 33 is sized to freely and slidingly receive a threaded rod 36 (shown in FIG. 3) extending from the distal end of the carriage assembly 40, as described below. The enlarged bore 35 has a smooth interior surface and has an inner diameter slightly larger than the outer diameter of the threaded rod 36 (a longitudinal cross-section of the threaded rod positioned inside of the enlarged bore is shown in FIG. 5).

The carriage assembly 40 includes a main body 41 and the threaded rod 36 extending distally therefrom along the longitudinal axis of the outer frame 30. The threaded rod 36 preferably is longer than the anticipated maximum travel distance of the carriage assembly 40 within the elongated space 34 (e.g., at least about 50 mm), such that the threaded rod 36 does not fully withdraw from the enlarged bore 35 during deployment of the prosthetic valve.

A deployment actuator 21 is threadedly engaged with the threaded rod 36. The deployment actuator is positioned in abutting relationship with the end member 33 of the frame 30 so that rotation of the actuator in one direction (either clockwise or counterclockwise depending on the orientation of the threads on the threaded rod 36) causes the threaded rod and the carriage assembly 40 to move proximally within the elongated space 34. Rotation of the deployment actuator 21 in the opposite direction, however, does not cause translational movement of carriage assembly 40, but rather simply causes the deployment actuator to threadedly advance on the threaded rod 36 as it moves away from the end member 33 of the frame 30. Although the movement of the deployment actuator 21 away from the end member 33 of the frame 30 enables the carriage assembly 40 to move distally until the deployment actuator again contacts the distal end member 33 of the frame, such movement is not easily controllable, but rather is subject to the "touch and feel" of the user.

In a variant of the embodiment described above, the deployment actuator 21 may be longitudinally constrained relative to the frame 30, for example, by the engagement of an annular rib on the distal end of the deployment actuator with an annular groove in the bore 35 so that the deployment actuator 21 may rotate in either direction without moving away from the distal end member 33 of the frame. Rather than an annular rib and an annular groove, any mechanism may be used for longitudinally fixing the deployment actuator 21 relative to the distal end 33 of the frame 30 so as to permit rotation of the deployment actuator in both directions without translation of same within the space 34. Such an arrangement would provide a user with the ability to carefully control movement of the carriage assembly 40 both proximally within the space 34 during a valve deployment operation, and distally within the space 34 during a resheathing operation, as described more fully below.

Figure 6:
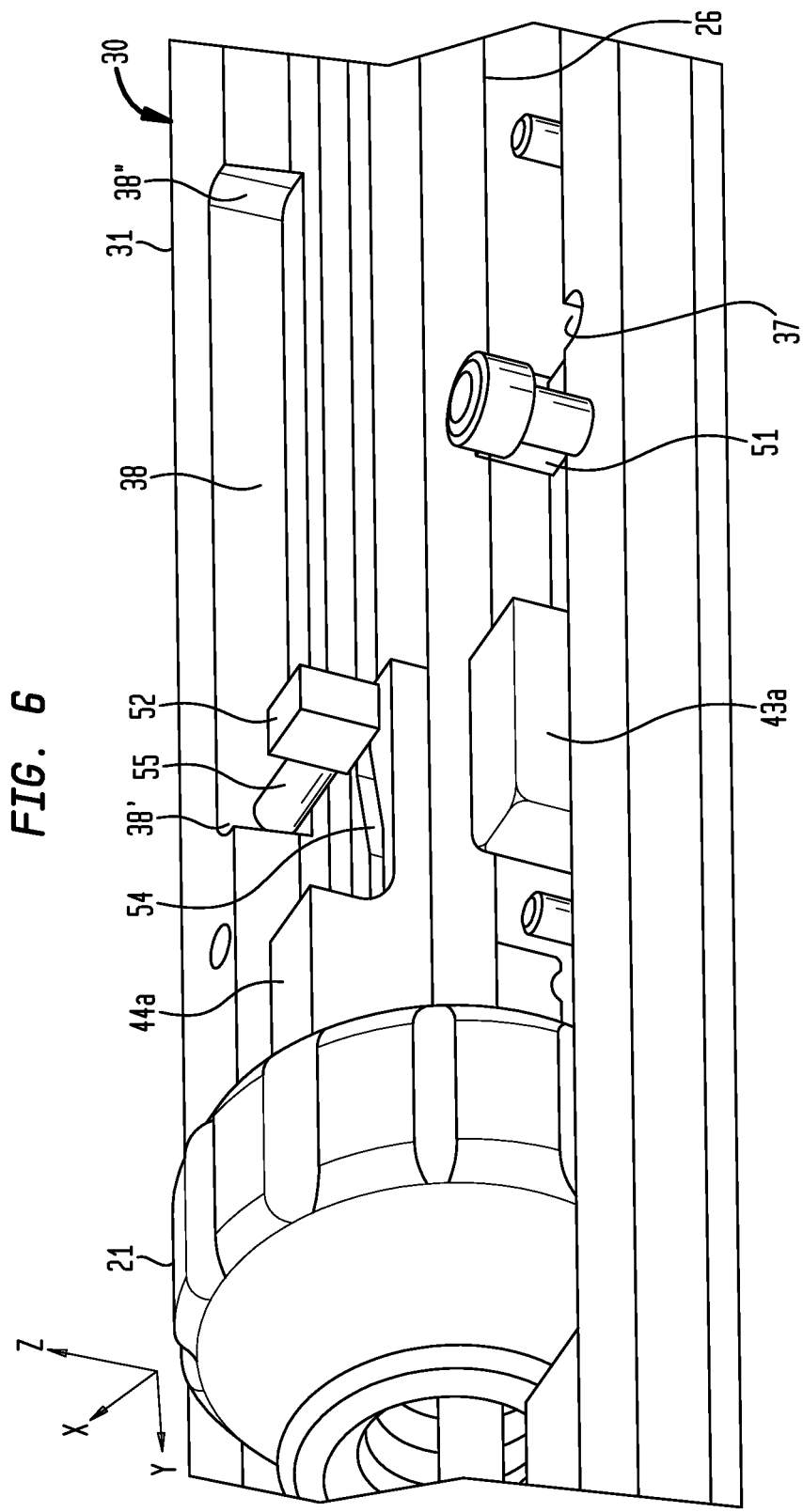
FIG. 6 is an enlarged perspective view of a portion of the handle of FIG. 1, shown without the inner frame.
Figure 7:
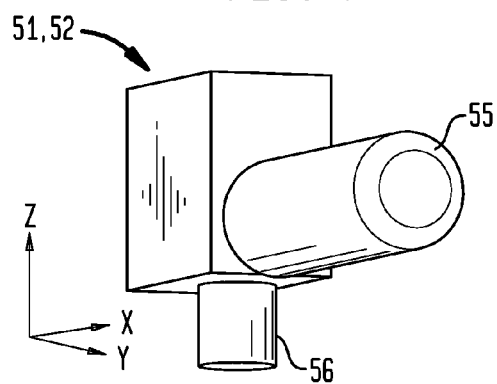
FIG. 7 is a perspective view of the locking member of the handle shown in FIG. 6.

Referring now to FIGS. 5-7, the carriage assembly 40 includes a deployment lock 43 adapted to prevent any movement of the carriage assembly within the frame 30, thereby preventing a user from accidentally initiating deployment of a prosthetic valve. The deployment lock 43 includes a control member 49 that is longitudinally slidable in a slot 45 between a distal position (shown in FIG. 5) and a proximal position (not shown). The control member 49 includes a cam slot 53 disposed in its upper surface, the distal end of the cam slot being spaced farther from the adjacent side rail 31 than the proximal end thereof. A locking member 51 includes a downwardly projecting pin 56 which travels in the cam slot 53. The locking member 51 also has a laterally projecting pin 55 which extends through an aperture 47 in the main body 41. With the carriage assembly 40 in its initial position, the aperture 47 is aligned with a recess 37 in the side rail 31 of the frame 30. When the control member 49 is in its distalmost or locked position (shown in FIG. 5), the pin 56 of the locking member 51 will be at the proximal end of the cam slot 53, such that the pin 55 will extend through the aperture 47 and into the recess 37, thus locking the carriage assembly 40 from any longitudinal movement relative to the frame 30. Movement of the control member 49 proximally to an unlocked position causes the pin 56 of the locking member 51 to move toward the distal end of the cam slot 53, thereby moving the locking member laterally inward until the pin 55 is no longer engaged in the recess 37. This action thus frees the carriage assembly 40 for longitudinal movement relative to the frame 30.

The carriage assembly 40 also includes a resheathing lock 44 adapted to limit the longitudinal movement of the carriage assembly within the outer frame 30, thereby preventing a user from accidentally completing the deployment of a prosthetic valve. The resheathing lock 44 includes a control member 50 that is longitudinally slidable in a slot 46 between a distal position (shown in FIG. 5) and a proximal position (not shown). The control member 50 includes a cam slot 54 disposed in its upper surface, the distal end of the cam slot being spaced farther from the adjacent side rail 31 than the proximal end thereof. A locking member 52 includes a downwardly projecting pin 56 which travels in the cam slot 54. The locking member 52 also has a laterally projecting pin 55 which extends through an aperture 48 in the main body 41. With the carriage assembly 40 in its initial position, the aperture 48 is aligned with the distal end 38' of a longitudinally extending slot 38 in the side rail 31 of the frame 30. When the control member 50 is in its distalmost position (shown in FIG. 5), the pin 56 of the locking member 52 will be at the proximal end of the cam slot 54, such that the pin 55 will extend through the aperture 48 and into the slot 38. Such condition will enable the carriage assembly to move longitudinally within the frame 30 between an initial position at which the pin 55 contacts the distal end 38' of the slot 38 and a position at which the pin 55 contacts the proximal end 38" of the slot 38. Movement of the control member 50 proximally causes the pin 56 of the locking member 52 to move toward the distal end of the cam slot 54, thereby moving the locking member laterally inward until the pin 55 is no longer engaged in the slot 38. This action thus frees the carriage assembly 40 for further proximal movement relative to the frame 30, thereby permitting full deployment of a prosthetic valve from the compartment 23 of the catheter assembly 16.

The slot 38 has a length L1 between the distal end 38' and the proximal end 38" that is slightly greater than the initial distance that the carriage assembly 40 may travel while still permitting resheathing of the valve contained in the compartment 23. More particularly, the length L1 is equal to this initial travel distance plus the diameter of the pin 55. As a result, when the resheathing lock 44 is in the locked position, the carriage assembly 40 can move proximally relative to the frame 30 only by this amount.

The initial distance that the carriage assembly 40 can travel before being limited by the proximal end 38" of the slot 38 may depend on the structure of the particular prosthetic valve to be deployed. Preferably, the initial travel distance of the carriage assembly 40 is about 3 mm to about 5 mm less than the crimped valve length. Alternatively, the initial travel distance of the carriage assembly 40 may be about 40 mm to about 45 mm, which is about 80% to about 90% of the length of an exemplary 50 mm valve. In other arrangements, the initial distance that the carriage assembly 40 can travel and/or the length of the slot 38 can be determined as a percentage of the length of the prosthetic valve and/or of the compartment 23, including, for example, 50%, 60%, 70%, 75%, 85%, or 95%.

The operation of the delivery device 10 to deploy a prosthetic valve will now be described. To load the delivery device 10 with a collapsible prosthetic valve, a user can retract the distal sheath 24 to expose the compartment 23, place the valve around the inner shaft 26, couple the proximal end of the valve to the retainer 25, compresses or crimp the valve, and slide the distal sheath 24 back over the compartment, which holds the valve in a compressed state. In this starting condition, the handle 20 will be in an initial state with the carriage assembly 40 at its distalmost position within the frame 30, the deployment lock 43 will be in its locked position to prevent accidental deployment, and the resheathing lock 44 will be in its locked position to prevent full deployment once the deployment lock 43 has been unlocked.

To use the operating handle 20 to deploy a prosthetic valve that has been compressed and inserted in the compartment 23 and covered by the distal sheath 24, a user will initially move the deployment lock 43 to its unlocked position, thereby freeing the carriage assembly 40 for longitudinal movement. The user can then rotate the deployment actuator 21, causing the carriage assembly 40 to slide proximally within the elongated space 34 in frame 30. Because the distal sheath 24 is affixed to the outer shaft 22, which in turn is affixed to the carriage assembly 40, and because the inner shaft 26 is affixed to the frame 30, sliding the carriage assembly proximally relative to the frame will retract the distal sheath proximally from the compartment 23, thereby exposing and initiating deployment of the valve located therein.

It will be appreciated that the user can initiate the deployment process without use of the deployment actuator 21 by simply grasping the carriage assembly 40 and pulling same proximally within the frame 30. Such action requires significant pulling force in order to overcome the frictional forces acting on the outer shaft 22 and the distal sheath 24. For that reason, the use of the deployment actuator 21 to retract the distal sheath 24 is preferred since such use provides the user with a mechanical advantage to overcome the aforementioned frictional forces, thereby providing the user with much greater control of the deployment process.

In any event, since the resheathing lock 44 is in the locked position, movement of the carriage assembly 40 proximally may continue only until the pin 55 of the locking member 52 contacts the proximal end 38" of the slot 38. At this point, the distal sheath 24 will not be fully withdrawn from the compartment 23, and the prosthetic valve will not be fully deployed.

When the deployment procedure has reached this juncture, the user can evaluate the position of the valve and determine whether the annulus end of the valve is properly aligned relative to the patient's aortic annulus. If repositioning is desired, the user may resheathe the valve by sliding the carriage assembly 40 distally within the frame 30, thereby moving the distal sheath 24 distally over the compartment 23 and the partially deployed valve and recollapsing the expanded part of the stent portion of the valve. This may be accomplished by rotating the deployment actuator 21 to advance it proximally on the threaded rod 36 and simply pushing the carriage assembly 40 in the distal direction or, in the variant embodiment in which the deployment actuator 21 is longitudinally fixed relative to the distal end member 33 of the frame 30, by rotating the deployment actuator in the direction opposite that used for deployment. Such rotation will cause the threaded rod 36 to progress distally through the deployment actuator 21 until the carriage assembly 40 has reached the starting condition shown in FIG. 5. With the valve resheathed, the user can reposition the catheter assembly 16 and commence the deployment procedure once again.

Once the valve has been properly positioned relative to the aortic annulus, the user may complete the deployment process. To do so, the user slides the resheathing lock 44 from the locked position to the unlocked position, thereby retracting the pin 55 of locking member 52 so that the carriage assembly 40 is free to continue its movement proximally within the frame 30. The user can complete the deployment of the valve by continuing to slide the carriage assembly 40 proximally, for example, by rotating the deployment actuator 21. When the valve has been unsheathed, the stent portion of the valve self-expands and disengages from the retainer 25, thereby releasing the valve from the catheter assembly 16.

Figure 8:
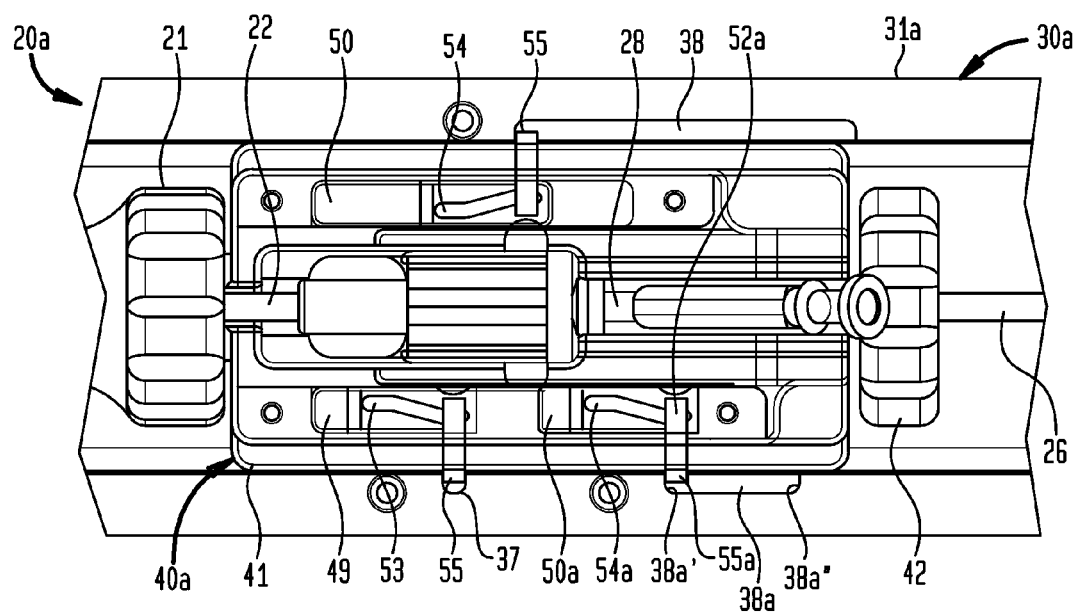
FIG. 8 is an enlarged bottom plan view of a portion of a handle in accordance with another embodiment of the invention, suitable for use with the transfemoral catheter assembly of FIG. 1.

Referring now to FIG. 8, a portion of an operating handle 20*a* in accordance with another embodiment of the invention is shown. The operating handle 20*a* is suitable for use with the catheter assembly 16 described above with reference to FIG. 1. The operating handle 20*a* is similar to the operating handle 20 described above, but differs in that it includes a second resheathing lock 44*a* in addition to the first resheathing lock 44. Hence, the operating handle 20*a* is capable of limiting the proximal movement of the carriage assembly 40*a* at two separate locations, rather than at a single location. The carriage assembly 40*a* is similar to the carriage assembly 40 shown in FIGS. 1-5, except for the addition of the second resheathing lock 44*a*.

The frame 30*a* of the operating handle 20*a* is similar to the frame 30 shown in FIGS. 1, 2, and 4-6, except that the side rail 31*a* on the side opposite resheathing lock 44 includes a second resheathing slot 38*a*. The slot 38*a* has a length between its distal end 38*a*' and its proximal end 38*a*" that is slightly greater than an initial distance that the carriage assembly 40*a* may travel to effect a partial deployment of the prosthetic valve. More particularly, the length of the slot 38*a* is equal to this initial travel distance plus the diameter of the pin 55*a* in the second resheathing lock 44*a*. As a result, when the second resheathing lock 44*a* is in the locked position, the carriage assembly 40*a* can move proximally relative to the frame 30*a* only by this amount. Preferably, this initial travel distance of the carriage assembly 40*a* is about 25 mm, or about half of the length of a conventional prosthetic aortic valve. In other arrangements, this initial travel distance may be about 40% to about 60% of the length of a conventional prosthetic aortic valve.

The valve deployment process using the operating handle 20*a* is similar to the deployment process described above in connection with the operating handle 20, except for the use of the second resheathing lock 44*a*. Thus, to use the operating handle 20*a* to deploy a prosthetic valve from compartment 23 of the catheter assembly 16, the user can first move the deployment lock 43 to an unlocked position, thereby freeing carriage assembly 40*a* for proximal movement relative to the frame 30*a*. With the deployment lock 43 in the unlocked position, the user can rotate the deployment actuator 21 to move the carriage assembly 40*a* proximally until the lateral pin 55*a* of resheathing lock 44*a* contacts the proximal end 38*a*" of the second resheathing slot 38*a*.

At this stage of deployment, while the second resheathing lock 44*a* is in the locked position, the user can decide to resheathe and reposition the valve. At about the halfway-unsheathed position, the valve may be partially functioning, such that the user can assess the valve position and decide whether to continue deployment or to resheathe and reposition the valve. If the position of the valve appears to be acceptable, the user can continue to the next stage of deployment by moving the second resheathing lock 44*a* to the unlocked position, freeing the carriage assembly 40*a* for further proximal movement within the frame 30*a*.

With the second resheathing lock 44*a* unlocked, the user can continue to rotate the deployment actuator 21 to further move the carriage assembly 40*a* proximally. However, since the resheathing lock 44 is in the locked position, the proximal movement of the carriage assembly 40*a* may continue only until the pin 55 of the locking member 52 contacts the proximal end 38" of the slot 38. At this point, the distal sheath 24 will not be fully withdrawn from the compartment 23, and the prosthetic valve will still not be fully deployed. Once again, the user may evaluate the position of the valve and determine whether repositioning is necessary. If repositioning is desired, the user may resheathe the valve by sliding the carriage assembly 40*a* distally within the frame 30*a* in the manner described above. On the other hand, if the valve position is acceptable, the user may unlock the resheathing lock 44 and complete the deployment of the valve by continuing to slide the carriage assembly 40*a* proximally, such as by rotating the deployment actuator 21.

Figure 9:
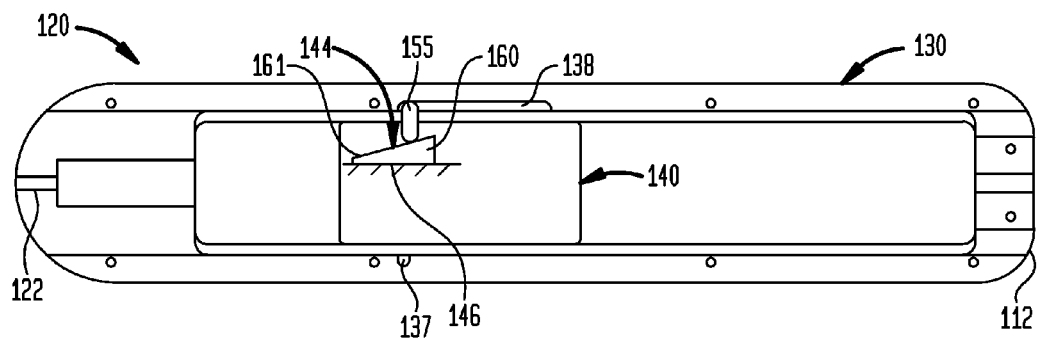
FIG. 9 is a diagrammatic top plan view of another embodiment of a handle suitable for use with the transfemoral catheter assembly of FIG. 1.

Referring now to FIG. 9, an operating handle 120 in accordance with another embodiment of the invention is shown. The operating handle 120 is suitable for use with the catheter assembly 16 described above with reference to FIG. 1. The operating handle 120 is similar to the operating handle 20 described above with reference to FIGS. 1-7, but differs in the structure of the deployment lock and the resheathing lock, although these locks function in substantially the same way as described above.

The operating handle 120 includes a carriage assembly 140 having a resheathing lock 144 that controls the lateral retraction of a locking pin 155. The resheathing lock 144 includes a cam member 160 that is slidably mounted in an elongated slot 146. The cam member 160 has a tapered surface 161, such that when the cam member is slid proximally in the slot 146, the locking pin 155 retracts in a lateral direction out of the slot 138, thereby permitting the carriage assembly 140 to continue proximally past the limit set by the proximal end of slot 138 and enabling the valve to be fully deployed.

Although the retraction mechanism for the locking pin 155 is not shown in FIG. 9, when the resheathing lock 144 is slid proximally, the locking pin 155 maintains contact with the tapered surface 161 of the resheathing lock, thereby pulling the locking pin 155 out of engagement with the slot 138. For example, a perpendicularly protruding portion of the locking pin 155 may travel in a slot (similar to how the pin 56 travels in the cam slot 54) that forces the locking pin 155 to maintain contact with the tapered surface of the resheathing lock 144. Alternatively, the pin 155 may be inwardly biased by a spring, such that the pin is pulled out of the slot 138 by the spring as the cam member 160 is slid proximally in the slot 146. Other arrangements for retracting the locking pin 155 will be known to the skilled artisan and may be used herewith.

Although a deployment locking mechanism is not shown in FIG. 9, a deployment lock similar in structure to the resheathing lock 144 can be included that is capable of engaging and withdrawing a second locking pin into and out of the recess 137 located in the frame side rail opposite the slot 138.

Figure 10:
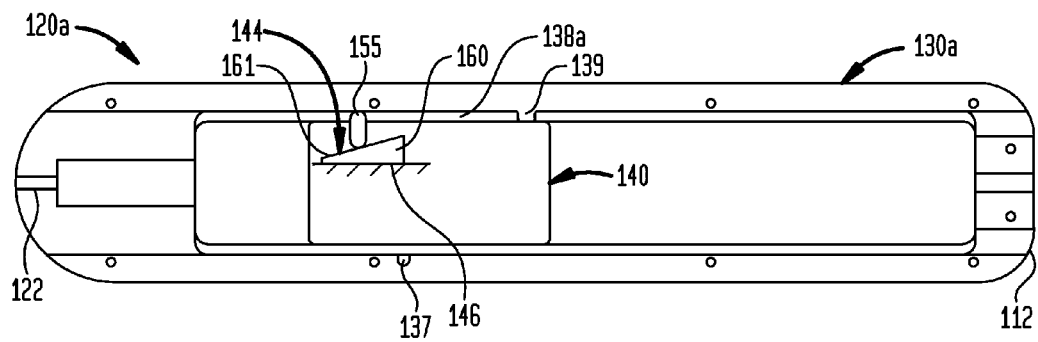
FIG. 10 is a diagrammatic top plan view of another embodiment of a handle suitable for use with the transfemoral catheter assembly of FIG. 1.

Referring now to FIG. 10, an operating handle 120a in accordance with yet another embodiment of the invention is shown. The operating handle 120a is similar to the operating handle 120 described above, but differs in the structure of the resheathing lock, although the functioning of the resheathing lock is similar to that of the resheathing lock 44 of operating handle 20.

Rather than having a resheathing lock mechanism that includes a slot that is closed on both ends, such as the slot 38 described above in connection with the operating handle 20, the operating handle 120a has a frame 130a that includes a protuberance 139 that defines the proximal end of a recess 138a that is open on the distal end. The protuberance 139 is positioned on the frame 130a in substantially the same position as the proximal end 38" of the slot 38 is positioned in the operating handle 20.

During staged deployment of a prosthetic valve, when the locking pin 155 contacts the protuberance 139, the proximal movement of the carriage assembly 140 is stopped. While the resheathing lock 144 is in the locked position (shown in FIG. 10), the valve can be resheathed and repositioned if desired. When it is desired to fully deploy the valve, the user can unlock the resheathing lock 144 by sliding the cam member 160 proximally in the slot 146 to retract the locking pin 155 from the recess 138a so that the protuberance 139 no longer limits the proximal movement of the carriage assembly 140. The carriage assembly 140 is thus free to further move proximally and enable the valve to be fully deployed.

Figure 11:
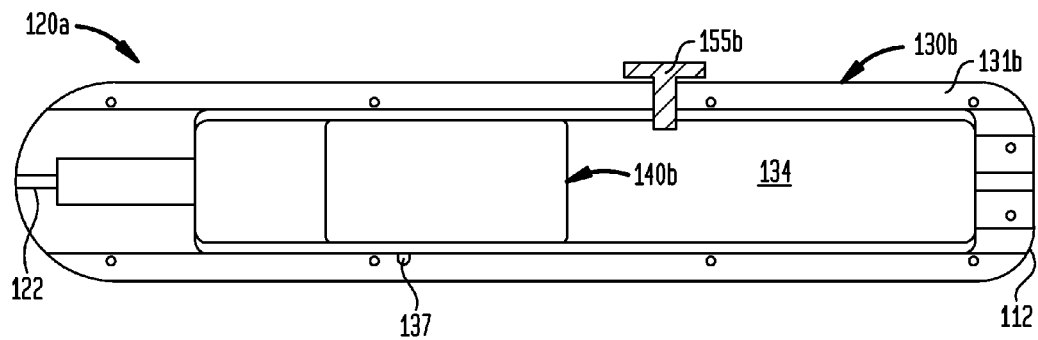
FIG. 11 is a diagrammatic top plan view of another embodiment of a handle suitable for use with the transfemoral catheter assembly of FIG. 1.

Referring now to FIG. 11, an operating handle 120b in accordance with a still further embodiment of the invention is shown. The operating handle 120b is similar to the operating handles 120 and 120a described above, but differs in the structure of the resheathing lock, although the functioning of the resheathing lock is similar to that of the resheathing lock 44 of the operating handle 20.

Rather than having a resheathing lock that includes a slot that is closed on both ends, such as the slot 38 described above in connection with the operating handle 20, or a recess that is closed on one end, such as the recess 138a described above in connection with the operating handle 120a, the operating handle 120b includes a carriage assembly 140b and a resheathing lock member 155b that projects through the side rail 131b of the frame 130b and into the elongated space 134 so as to obstruct the path of travel of the carriage assembly 140b in the proximal direction. As such, the resheathing lock member 155b defines the initial distance that the carriage assembly 140b may travel before full deployment of the valve occurs. The resheathing lock member 155b may be moved to an unlocked position by retracting the lock member by a sufficient amount that it no longer protrudes into the space 134. With the resheathing lock member 155b in the unlocked position, the carriage assembly 140b may continue to move proximally, thereby allowing for full deployment of the valve. Optionally, the locking member 155b may be designed to be fully removable from the frame 130b and disposable.

Referring now to FIG. 12, an exemplary transapical delivery device 210 for a collapsible prosthetic heart valve (or other types of self-expanding collapsible stents) has a catheter assembly 216 for delivering the heart valve to and deploying the heart valve at a target location, and an operating handle 220 for controlling deployment of the valve from the catheter assembly. The delivery device 210 extends from a proximal end 212 to a distal tip 214. The catheter assembly 216 is adapted to receive a collapsible prosthetic heart valve (not shown) in a compartment 223 defined around a tubular support shaft 221 and covered by a distal sheath 224.

The support shaft 221 extends between a pair of spaced retainers 225 and 227 affixed thereto and defining the ends of the compartment 223. A collapsible prosthetic valve may be assembled around the support shaft 221 and between the retainers 225 and 227 in the compartment 223.

The distal sheath 224 surrounds the support shaft 221 and is slidable relative to the support shaft such that it can selectively cover or uncover the compartment 223. The distal sheath 224 is affixed at its distal end to the distal tip 214, and its proximal end 229 abuts the retainer 227 when the distal sheath is fully covering the compartment 223, as shown in FIG. 12. The proximal end 229 of the distal sheath 224 is spaced apart from the retainer 227 when the compartment 223 is at least partially uncovered.

The delivery device further includes an outer shaft 222, the proximal end of which is connected to the operating handle 220, and the distal end of which is connected to the retainer 227. An inner shaft 226 extends through the operating handle 220 and the support shaft 221 to the distal tip 214. The connection of the distal sheath 224 to the distal tip 214 thus enables the inner shaft 226 to control the movement of the distal sheath both proximally and distally.

The operating handle 220 is adapted to control deployment of a prosthetic valve located in the compartment 223 by permitting a user to selectively slide the inner shaft 226 and the attached distal sheath 224 distally or proximally relative to the support shaft 221, thereby respectively uncovering or covering the compartment with the distal sheath. The proximal end of the outer shaft 222 is affixed to an outer frame 230 of the operating handle 220, and the proximal end of the inner shaft 226 is affixed to a carriage assembly 240 of the operating handle that is slidable along a longitudinal axis of the frame, such that a user can selectively slide the inner shaft relative to the outer shaft by sliding the carriage assembly relative to the frame. A hemostasis valve 228 provides an internal gasket adapted to create a seal between the inner shaft 226 and the proximal end of the outer shaft 222. The strength of this seal may be adjusted by a gasket adjustment wheel 242 that functions in substantially the same manner as the adjustment wheel 42 described above.

The frame 230 includes a pair of side rails 231 joined at the proximal end 212 by an end member 232 and joined at the distal end by an end member 233. Collectively, the side rails 231, the end member 232, and the end member 233 define an elongated space 234 in the frame 230 in which the carriage assembly 240 may travel.

The carriage assembly 240 is shown in FIG. 12 without a threaded rod or a deployment actuator, such as described above in connection with the operating handle 20. However, it will be appreciated that the operating handle 220 may have the same components as are provided at the distal end member 33 of operating handle 20, but these components would be arranged at the proximal end 212 of the handle 220. That is, the proximal end member 232 of the operating handle 220 may have an enlarged bore sized to slidingly receive a threaded rod extending from the proximal end of the carriage assembly 240. A deployment actuator may be threadedly assembled on the threaded rod between the carriage assembly 240 and the proximal end member 232 of the frame 230 such that rotation of the deployment actuator controllably urges the carriage assembly distally within the elongated space 234.

Moreover, the deployment actuator may be longitudinally fixed relative to the proximal end member 232 such that rotation of the deployment actuator in the opposite direction causes the carriage assembly 240 to move proximally relative to the frame 230.

The operating handle 220 may also include one or more lock mechanisms adapted to prevent accidental partial or full deployment of a prosthetic valve located in the compartment 223. Thus, as with all of the operating handles described above, the operating handle 220 may include a deployment lock for preventing a user from accidentally initiating deployment of a valve, as well as a resheathing lock for preventing the user from accidentally completing deployment of the valve. The structures of these lock mechanisms may be similar to the structures of any of the lock mechanisms described above, but modified to limit the movement of the carriage assembly 240 distally relative to the frame 230. For example, the lock mechanism may be similar to that included in the operating handle 120b shown and described with reference to FIG. 11, except that the resheathing lock member 255 that projects through the side rail 231 of the frame 230 and into the elongated space 234 is located distally of the carriage assembly 240 (as opposed to proximally as in FIG. 11). Thus, the resheathing lock member 255 defines the initial distance which the carriage assembly 240 may travel in the distal direction before full deployment of the valve occurs.

The operation of the operating handle 220 to deploy a prosthetic valve from the compartment 223 is similar to the operation of the operating handle 20 described above with reference to FIGS. 1-7, except that the operating handle 220, as shown, does not include a deployment actuator to provide the user with mechanical advantage. After moving the deployment lock, if any, to an unlocked condition, the user can grasp the carriage assembly 240 and push the same distally within the elongated space 234 in the frame 230, which thereby pushes the distal sheath 224 distally relative to the compartment 223 and exposes and initiates deployment of the valve located therein.

Since the resheathing lock member 255 is in the locked position, movement of the carriage assembly 240 distally may continue only until the distal end of the carriage assembly contacts the lock member. At this juncture, the distal sheath 224 will not fully uncover the compartment 223, and the prosthetic valve will not be fully deployed. Therefore, if the user desires to resheathe and reposition the valve before full deployment, the user can do so by grasping the carriage assembly 240 and sliding it proximally within the frame 230 until the carriage assembly contacts the proximal end 232 of the frame. Once the valve has been properly positioned, the deployment operation may be completed by withdrawing the resheathing lock member 255 to the unlocked position and moving the carriage assembly 240 further distally until the valve is fully deployed.

Although the operating handles have been described herein as having one or two resheathing locks, any number of resheathing locks may be used, with or without a deployment lock, resulting in any number of stages in the deployment process. For example, there may be three, four, five, six or more resheathing locks, which thus enable the deployment procedure to be controlled incrementally.

More particularly, if a user desires, for example, a two-stage deployment process, a single resheathing lock may be used, resulting in an unsheathing of perhaps about 80% to about 90% of the valve in a first deployment stage, followed by an unsheathing of the remaining about 10% to about 20% of the valve in a second deployment stage.

If the user desires a three-stage deployment process, on the other hand, a single resheathing lock may be used with a deployment lock, resulting in a first deployment stage in which no deployment can occur, a second deployment stage in which, for example, about 80% to about 90% of the valve is unsheathed, and a third deployment stage in which the remaining about 10% to about 20% of the valve is unsheathed.

Still further, if the user desires a four-stage deployment process, two resheathing locks may be used with a deployment lock, resulting in a first deployment stage in which no deployment can occur, a second deployment stage in which, for example, about 50% of the valve is unsheathed, a third deployment stage in which, for example, about 80% to about 90% of the valve is unsheathed, and a fourth deployment stage in which the remaining about 10% to about 20% of the valve is unsheathed. This last process may be modified to a three-stage deployment process by omitting the deployment lock while keeping the two resheathing locks.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A delivery device for a collapsible prosthetic heart valve, the delivery device comprising:
    an operating handle, including:
        a frame defining a movement space therein;
        a carriage assembly moveable in a longitudinal direction within the movement space; and
        a first resheathing lock having a locked position and an unlocked position, the first resheathing lock in the locked position limiting movement of the carriage assembly in the longitudinal direction to a first intermediate position in the movement space, and the first resheathing lock in the unlocked position permitting movement of the carriage assembly in the longitudinal direction beyond the first intermediate position in the movement space; and
    a catheter assembly, including:
        a first shaft around which a compartment is defined, the first shaft being fixedly connected to one of the frame or the carriage assembly, the compartment being adapted to receive the valve in an assembled condition; and
        a distal sheath operatively connected to the carriage assembly, the distal sheath being moveable between a closed condition adapted to maintain the valve in the assembled condition and an open condition adapted to fully deploy the valve,
    wherein movement of the carriage assembly to the first intermediate position moves the distal sheath to a condition between the closed condition and the open condition so that the valve is not fully deployed, and
    wherein the first shaft is fixedly connected to the carriage assembly, and the catheter assembly further includes an outer shaft connecting the frame to the compartment and at least partially surrounding the first shaft.

2. The delivery device of claim 1, wherein the operating handle further includes a deployment lock moveable between a locked position and an unlocked position, the deployment lock in the locked position preventing movement of the carriage assembly in the longitudinal direction within the movement space, the deployment lock in the unlocked position permitting movement of the carriage assembly in the longitudinal direction within the movement space.

3. The delivery device of claim 1, wherein the carriage assembly includes a threaded rod and the operating handle further includes a deployment actuator threadedly engaged with the threaded rod such that rotation of the deployment actuator moves the carriage assembly in the longitudinal direction in the movement space.

4. The delivery device of claim 1, wherein the compartment defines a first length and the first intermediate position in the movement space corresponds to a travel distance of the carriage assembly, the travel distance being less than the first length.

5. The delivery device of claim 4, wherein the collapsible prosthetic heart valve defines a second length and the travel distance is about 80% to about 90% of the second length.

6. The delivery device of claim 4, wherein the collapsible prosthetic heart valve defines a second length and the travel distance is about 80% to about 90% of the second length.

7. The delivery device of claim 1, wherein the operating handle further includes a second resheathing lock moveable between a locked position and an unlocked position, the second resheathing lock in the locked position limiting movement of the carriage assembly in the longitudinal direction to a second intermediate position in the movement space, the second resheathing lock in the unlocked position permitting movement of the carriage assembly in the longitudinal direction beyond the second intermediate position.

8. The delivery device of claim 7, wherein the collapsible prosthetic heart valve defines a length, the second intermediate position defines a first travel distance, and the first intermediate position defines a second travel distance, the first travel distance being about 40% to about 60% of the length and the second travel distance being about 80% to about 90% of the length.

9. The delivery device of claim 7, wherein the collapsible prosthetic heart valve defines a length, the second intermediate position defines a first travel distance, and the first intermediate position defines a second travel distance, the first travel distance being about 40% to about 60% of the length and the second travel distance being about 80% to about 90% of the length.

10. A delivery device for a collapsible prosthetic heart valve, the delivery device comprising:
an operating handle, including:
a frame defining a movement space therein;
a carriage assembly moveable in a longitudinal direction within the movement space; and
a first resheathing lock having a locked position and an unlocked position, the first resheathing lock in the locked position limiting movement of the carriage assembly in the longitudinal direction to a first intermediate position in the movement space, and the first resheathing lock in the unlocked position permitting movement of the carriage assembly in the longitudinal direction beyond the first intermediate position in the movement space; and
a catheter assembly, including:

a first shaft around which a compartment is defined, the first shaft being fixedly connected to one of the frame or the carriage assembly, the compartment being adapted to receive the valve in an assembled condition; and
a distal sheath operatively connected to the carriage assembly, the distal sheath being moveable between a closed condition adapted to maintain the valve in the assembled condition and an open condition adapted to fully deploy the valve,
wherein movement of the carriage assembly to the first intermediate position moves the distal sheath to a condition between the closed condition and the open condition so that the valve is not fully deployed, and
wherein the frame includes a slot and the first resheathing lock includes a retractable locking member that is engaged in the slot when the first resheathing lock is in the locked position, an end of the slot defining the first intermediate position.

11. The delivery device of claim 10, wherein the first shaft is fixedly connected to the frame, the catheter assembly further including an outer shaft connecting the carriage assembly to the distal sheath and at least partially surrounding the first shaft.

12. The delivery device of claim 10, wherein the operating handle further includes a deployment lock moveable between a locked position and an unlocked position, the deployment lock in the locked position preventing movement of the carriage assembly in the longitudinal direction within the movement space, the deployment lock in the unlocked position permitting movement of the carriage assembly in the longitudinal direction within the movement space.

13. The delivery device of claim 10, wherein the carriage assembly includes a threaded rod and the operating handle further includes a deployment actuator threadedly engaged with the threaded rod such that rotation of the deployment actuator moves the carriage assembly in the longitudinal direction in the movement space.

14. The delivery device of claim 10, wherein the compartment defines a first length and the first intermediate position in the movement space corresponds to a travel distance of the carriage assembly, the travel distance being less than the first length.

15. The delivery device of claim 10, wherein the operating handle further includes a second resheathing lock moveable between a locked position and an unlocked position, the second resheathing lock in the locked position limiting movement of the carriage assembly in the longitudinal direction to a second intermediate position in the movement space, the second resheathing lock in the unlocked position permitting movement of the carriage assembly in the longitudinal direction beyond the second intermediate position.

16. A system for delivery of a collapsible prosthetic heart valve, the system comprising:
a collapsible prosthetic heart valve;
an operating handle, including:
a frame defining a first longitudinal end and a second longitudinal end spaced apart in a longitudinal direction of the operating handle, and a movement space located between the first and second longitudinal ends;
a carriage assembly having a first longitudinal end and a second longitudinal end spaced apart in the longitudinal direction, the carriage assembly moveable in the longitudinal direction within the movement space, the first and second longitudinal ends of the carriage assembly located within the movement space; and a first resheathing lock having a locked position and an unlocked position, the resheathing lock in the locked position limiting movement of the carriage assembly in the longitudinal direction to a first intermediate position in the movement space, and the first resheathing lock in the unlocked position permitting movement of the carriage assembly in the longitudinal direction beyond the first intermediate position in the movement space; and a catheter assembly, including:
- a first shaft around which a compartment is defined, the first shaft being fixedly connected to one of the frame or the carriage assembly, the valve being mounted in the compartment in an assembled condition; and
- a distal sheath operatively connected to the carriage assembly, the distal sheath being moveable between a closed condition adapted to maintain the valve in the assembled condition and an open condition adapted to fully deploy the valve, wherein movement of the carriage assembly to the first intermediate position moves the distal sheath to a condition between the closed condition and the open condition so that the valve is not fully deployed, and wherein the first shaft is fixedly connected to the carriage assembly, and the catheter assembly further includes an outer shaft connecting the frame to the compartment and at least partially surrounding the first shaft.

17. The system of claim 16, wherein the collapsible prosthetic heart valve defines a length and the first intermediate position in the movement space corresponds to a travel distance of the carriage assembly, the travel distance being about 80% to about 90% of the length.

18. The system of claim 16, wherein the operating handle further includes a second resheathing lock moveable between a locked position and an unlocked position, the second resheathing lock in the locked position limiting movement of the carriage assembly in the longitudinal direction to a second intermediate position in the movement space, the second resheathing lock in the unlocked position permitting movement of the carriage assembly in the longitudinal direction beyond the second intermediate position.

19. The system of claim 18, wherein the collapsible prosthetic heart valve defines a length, the second intermediate position defines a first travel distance, and the first intermediate position defines a second travel distance, the first travel distance being about 40% to about 60% of the length and the second travel distance being about 80% to about 90% of the length.

* * * * *